United States Patent [19]

Martin

[11] Patent Number: 5,977,332
[45] Date of Patent: Nov. 2, 1999

[54] OLIGONUCLEOTIDES HAVING 2'-ETHER GROUPS

[75] Inventor: Pierre Martin, Rheinfelden, Switzerland

[73] Assignee: Novartis Corporation, Summit, N.J.

[21] Appl. No.: 09/026,713

[22] Filed: Feb. 20, 1998

Related U.S. Application Data

[62] Division of application No. 08/426,807, Apr. 20, 1995, Pat. No. 5,750,673.

[30] Foreign Application Priority Data

Apr. 27, 1994 [CH] Switzerland ............................ 1307/94

[51] Int. Cl.$^6$ .......................... C07H 21/00; C07H 21/04; A61K 31/70
[52] U.S. Cl. ........................ 536/23.1; 536/24.5; 536/24.3
[58] Field of Search .................................. 536/23.1, 24.5, 536/24.3

[56] References Cited

U.S. PATENT DOCUMENTS 5,750,673  5/1998  Martin ..................................... 536/26.1

FOREIGN PATENT DOCUMENTS

| 266099 | 5/1988 | European Pat. Off. . |
| 0626380 | 11/1994 | European Pat. Off. . |
| WO/8707300 | 12/1987 | WIPO . |
| WO/8908146 | 9/1989 | WIPO . |
| WO/9106556 | 5/1991 | WIPO . |

OTHER PUBLICATIONS

W. Müller, Institut fürPhysiologische Chemie, Abteilung "Angewandte Molekularbiologie", Universität, Duesbergweg, 6500 Mainz, W. Germany, pp. 274–279 (1979).
S. T. Crooke et al., Antisense Research and Applications Eds., CRC Press, Boca Raton, pp. 273–288, (1993).
G. Bott et al., J. Am. Chem. Soc., vol. 102, pp. 5618–5626 (1980).
A. Rossi, Institute Nazionale Tumori, pp. 409–436 (1979).
R.W. Sidwell, Research Professor of Biology and of Animal, Dairy and Veterinary Sciences, Utah State Univ., pp. 337–362 (1979).
F.M. Schabel, Jr., Southern Research Institute, Birmingham, Ala., pp. 363–394 (1979).
J.C. Martin, Nucleotide Analogues as Antiviral Agents, ACS Symposium Series 401, Table of Contents (1988).
W. Prusoff et al., Yale Univ. Sch. of Med. Dept. of Pharm. pp. 281–318 (1979).
T. Merigan et al., Stanford Univ. Div. of Infectious Diseases, pp. 395–407 (1979).
R. Walker et al., Nucleoside Analogues Chemistry, Biology and Medical Applications, Table of Contents (1979).
J.A. Martin et al., American Chemical Society, Design of Inhibitors of Herpes Simplex Virus Thymidine Kinase, Chapter 7, (1989).
V. E. Marquez, American Chemical Society, Design, Synthesis and Antiviral Activity of Nucleoside and Nucleotide Analogues, Chapter 10 (1989).
Frochler, BC et al. Tetrahedron Letters 34 (1993), pp. 1003–1006.
Lesnik, E.A. et al., Biochemistry 32 (1993), pp. 7832–7838.
Chemical Abstracts 122 (1995), abstract No. 56416V.
Beaucage, S.L., Iyer, R., Tetrahedron 48:2223–2311 (1992).
Matteucci, M.D., Bischofberger, N., Annual Reports in Medicinal Chemistry, 26: 287–296 (1991).
Hélène, C., Toulmé, J.J., Biochimica et Biophysica Acta 1049:99–125 (1990).
Marquez, V.E., Lim, M.I., Medicinal Research Reviews 6:1–40 (1986).
Uhlmann, E., Peyman A., Chemical Reviews, 90:543–584 (1990).
Sonveaux E., Bioorganic Chemistry 14:274–325 (1986).
Marky, L.A., Breslauer, K.J., Biopolymers 26:1601–1620 (1987).
Cook, P.D., Anti–Cancer Drug Design 6:585–607 (1991).
Uwe English et al., Angewandte Chemie Int. Ed. 30; pp. 613–722, (1991).

*Primary Examiner*—Gary L. Kunz
*Attorney, Agent, or Firm*—Gregory D. Ferraro

[57] ABSTRACT

Compounds of the formula

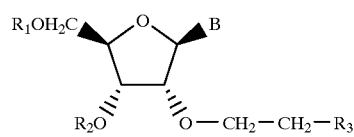

wherein $R_1$ and $R_2$ are each independently of the other hydrogen or a protecting group, or $R_1$ has those meanings and $R_2$ is a radical forming a phosphorus-containing nucleotide bridge group;

B is a purine or pyrimidine radical or an analogue thereof; and $R_3$ is OH, or F, and oligonucleotides that comprise those nucleosides are described.

14 Claims, No Drawings

OLIGONUCLEOTIDES HAVING 2'-ETHER GROUPS

This is a divisional application of U.S. application Ser. No. 08/426,807 filed: Apr. 20, 1995, now U.S. Pat. No. 5,750,673.

The invention relates to ribo-nucleoside analogues in which the 2'-OH group is etherified by hydroxyethyl or fluoroalkyl groups, to a process for the preparation thereof, to oligonucleotides comprising those nucleosides and to the use of the nucleosides for the preparation of oligonucleotides having identical or different nucleoside units in the molecule.

Nucleosides and oligonucleotides, both as anti-viral active ingredients and because of their ability to interact with nucleic acids ("anti-sense" oligonucleotides) and the biological activity associated therewith, have attracted a great deal of interest; see, for example, Uhlmann, E., Peyman, A., Chemical Reviews 90:543–584 (1990). In order to provide nucleosides having new properties or to improve the interaction of anti-sense oligonucleotides with natural nucleic acids and to improve their stability towards nucleases, the sugar residues of nucleosides (or of the nucleotide units in oligonucleotides), or the inter-nucleotide phosphate bond in oligonucleotides have been modified in a wide variety of ways; see, for example, Marquez, V. E., Lim, M. I., Medicinal Research Reviews 6:140 (1986), Hélène, C., Toulmé, J. J., Biochimica et Biophysica Acta 1049:99–125 (1990), Englisch, U., Gauss, D. H., Angewandte Chemie 103:629–646 (1991), Matteucci, M. D., Bischofberger, N., Annual Reports in Medicinal Chemistry 26:87–296 (1991). In Cook, P. D., Anti-Cancer Drug Design 6:585–607 (1991) and WO 91/06556, nucleosides that have been modified at the 2'-OH group of the sugar are described. The described modifications result in increased nuclease-resistance; the longer the alkyl radical becomes, the higher becomes the nuclease-resistance. With short alkyl radicals such as methyl, ethyl or propyl, a slight increase in binding affinity is observed while with longer chains the binding affinity falls off drastically. Nucleosides having hydroxyethyl or fluoroalkyl groups as side-chains of the 2'-OH group have never been incorporated in oligonucleotides until now. Surprisingly, the modifications according to the invention increase the binding affinity for complementary RNA in comparison with unsubstituted alkyl chains of the same length. This result was not to be expected on the basis of the published data. Analogously to the 2'-OH-modified oligoribonucleotides, the compounds according to the invention are similarly distinguished by a marked nuclease-resistance. In addition, oligonucleotides that comprise the nucleosides according to the invention show increased cellular uptake and consequently have improved bio-availability and activity in vivo.

The invention relates to compounds of formula I

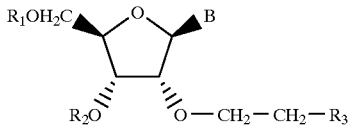

(I)

wherein $R_1$ and $R_2$ are each independently of the other hydrogen or a protecting group, or $R_1$ has those definitions and $R_2$ is a radical forming a phosphorus-containing nucleotide bridge group; B is a purine or pyrimidine radical or an analogue thereof; and $R_3$ is OH, F or $(CF_2)_nCF_3$ wherein n is a number from 0 to 7.

When $R_3$ is OH, this hydroxy group can be protected by a group defined for $R_1$ and $R_2$.

In a preferred form n is 0.

In a preferred form $R_1$ and $R_2$ are hydrogen.

Protecting groups and methods of derivatising the hydroxy groups with such protecting groups are generally known in sugar and nucleotide chemistry and are described, for example, by Greene, B. T., Protective Groups in Organic Synthesis, Wiley Interscience, New York (1991), by Sonveaux, E., Bioorganic Chemistry 14:274–325 (1986) or by Beaucage, S. L., Iyer, R., Tetrahedron 48:2223–2311 (1992). Examples of such protecting groups are: benzyl, methylbenzyl, dimethylbenzyl, methoxybenzyl, dimethoxybenzyl, bromobenzyl, 2,4-dichlorobenzyl; diphenylmethyl, di(methylphenyl)methyl, di(dimethylphenyl)methyl, di(methoxyphenyl)methyl, di(dimethoxyphenyl)methyl, triphenylmethyl, tris-4,4',4"-tert-butylphenylmethyl, di-p-anisylphenylmethyl, tri(methylphenyl)methyl, tri(dimethylphenyl)methyl, di(methoxyphenyl)(diphenyl)methyl, di(methoxyphenyl)phenylmethyl, tri(methoxyphenyl)methyl, tri(dimethoxyphenyl)methyl; triphenylsilyl, alkyldiphenylsilyl, dialkylphenylsilyl and trialkylsilyl having from 1 to 20, preferably from 1 to 12 and most preferably from 1 to 8 carbon atoms in the alkyl groups, for example trimethylsilyl, triethylsilyl, tri-n-propylsilyl, isopropyl-dimethylsilyl, tert-butyl-dimethylsilyl, tert-butyl-diphenylsilyl, n-octyl-dimethylsilyl, (1,1,2,2-tetramethylethyl)-dimethylsilyl; —$(C_1$–$C_8$alkyl$)_2$Si—O—Si$(C_1$–$C_8$alkyl$)_2$— wherein alkyl is, for example, methyl, ethyl, n-propyl, isopropyl, n-butyl, isobutyl or tert-butyl; $C_2$–$C_{12}$—, especially $C_2$–$C_8$-acyl, such as, for example, acetyl, propanoyl, butanoyl, pentanoyl, hexanoyl, benzoyl, methylbenzoyl, methoxybenzoyl, chlorobenzoyl and bromobenzoyl; $R_{S1}$-$SO_2$- wherein $R_{S1}$ is $C_1$–$C_{12}$alkyl, especially $C_1$–$C_6$alllyl, $C_5$- or $C_6$-cycloalkyl, phenyl, benzyl, $C_1$–$C_{12}$- and especially $C_1$–$C_4$-alkylphenyl, or $C_1$–$C_{12}$- and especially $C_1$–$C_4$-alkylbenzyl, or halophenyl or halobenzyl, for example methyl-, ethyl-, propyl-, butyl-, phenyl-, benzyl-, p-bromo-, p-methoxy and p-methylphenylsulfonyl; $C_1$–$C_{12}$-, preferably $C_1$–$C_8$-alkoxycarbonyl which is unsubstituted or substituted by F, Cl, Br, $C_1$–$C_4$alkoxy, tri-$(C_1$–$C_4$alkyl)silyl or by $C_1$–$C_4$alkylsulfonyl, for example methoxy-, ethoxy-, n-propoxy, isopropoxy-, n-butoxy-, isobutoxy- or tert-butoxy-carbonyl, 2-trimethylsilylethoxycarbonyl, 2-methylsulfonylethoxycarbonyl, allyloxycarbonyl, or phenyloxycarbonyl or benzyloxycarbonyl each unsubstituted or substituted as mentioned for alkoxycarbonyl, for example methyl- or methoxy- or chloro-phenyloxycarbonyl or -benzyloxycarbonyl, and 9-fluorenylmethyloxycarbonyl. When $R_1$ and/or $R_2$ are(is) alkyl, it may be substituted by F, Cl, Br, $C_1$–$C_4$alkoxy, phenyloxy, chlorophenyloxy, methoxyphenyloxy, benzyloxy, methoxybenzyloxy or by chlorophenyloxy. $R_1$ and $R_2$ in formula I may be identical or different protecting groups.

In an especially preferred form, $R_1$ and $R_2$ as protecting groups are benzyl, methylbenzyl, dimethylbenzyl, methoxybenzyl, dimethoxybenzyl, halogenated benzyl, especially bromobenzyl; diphenylmethyl, di(methylphenyl) methyl, di(dimethylphenyl)methyl, di(methoxyphenyl) methyl, di(methoxyphenyl)(phenyl)methyl, triphenylmethyl, tris-4,4',4"-tertbutylphenylmethyl, di-p-anisylphenylmethyl, tri(methylphenyl)methyl, tri (dimethylphenyl)methyl, tri(methoxyphenyl)methyl, tri (dimethoxyphenyl)methyl; trimethylsilyl, triethylsilyl, tri-n-propylsilyl, isopropyl-dimethylsilyl, tert-butyldimethylsilyl, tert-butyldiphenylsilyl, n-octyl-dimethylsilyl, (1,1,2,2-tetramethylethyl)-dimethylsilyl, —$(CH_3)_2Si$—O—$Si(CH_3)_2$—, —$(iso-C_3H_7)_2Si$—O—$Si(iso-C_3H_7)_2$—; acetyl, propanoyl, butanoyl, pentanoyl, hexanoyl, benzoyl, methylbenzoyl, methoxybenzoyl, chlorobenzoyl and bromobenzoyl; methyl-, ethyl-, propyl-, butyl-, phenyl-, benzyl-, p-bromo-, p-methoxy- and p-methylphenyl-sulfonyl; methoxy-, ethoxy-, n- or iso-propoxy- or n-, iso- or tertbutoxycarbonyl, or phenyloxycarbonyl, benzyloxycarbonyl, methyl- or methoxy- or chloro-phenyloxycarbonyl or -benzyloxycarbonyl or 9-fluorenylmethyloxycarbonyl.

$R_2$ as a phosphorus-containing radical forming a nucleotide bridge group may have the formula P1 or P2

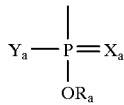

(P1)

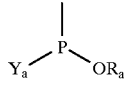

(P2)

wherein $Y_a$ is hydrogen, $C_1$–$C_{12}$alkyl, $C_6$–$C_{12}$aryl, $C_7$–$C_{20}$aralkyl, $C_7$–$C_{20}$alkaryl, —$OR_b$, —$SR_b$, —$NH_2$, primary amino, secondary amino, $O^\ominus M^\oplus$ or $S^\ominus M^\oplus$; $X_a$ is oxygen or sulfur; $R_a$ is hydrogen, $M^\oplus$, $C_1$–$C_{12}$alkyl, $C_2$–$C_{12}$alkenyl, $C_6$–$C_{12}$aryl, or the group $R_aO$— is N-heteroaryl-N-yl having 5 ring members and from 1 to 3 N atoms; $R_b$ is hydrogen, $C_1$–$C_{12}$alkyl or $C_6$–$C_{12}$aryl; and $M^\oplus$ is $Na^\oplus$, $K^\oplus$, $Li^\oplus$, $NH_4^\oplus$ or primary, secondary, tertiary or quaternary ammonium; alkyl, aryl, aralkyl and alkaryl in $Y_a$, $R_a$ and $R_b$ being unsubstituted or substituted by alkoxy, alkylthio, halogen, —CN, —$NO_2$, phenyl, nitrophenyl or by halophenyl.

$Y_a$ as primary amino contains preferably from 1 to 12 and most preferably from 1 to 6 carbon atoms, and, as secondary amino, contains preferably from 2 to 12 and most preferably from 2 to 6 carbon atoms.

The primary amino and secondary amino may, for example, be radicals of the formula $R_cR_dN$ wherein $R_c$ is H or, independently, has the definition of $R_d$, and $R_d$ is $C_1$–$C_{20}$—, preferably $C_1$–$C_{12}$— and most preferably $C_1$–$C_6$-alkyl, $C_1$–$C_{20}$—, preferably $C_1$–$C_{12}$— and most preferably $C_1$–$C_6$-aminoalkyl, $C_1$–$C_{20}$—, preferably $C_1$–$C_{12}$— and most preferably $C_1$–$C_6$-hydroxyalkyl; carboxyalkyl or carbalkoxyalkyl wherein the carbalkoxy group contains from 2 to 8 carbon atoms and the alkyl group from 1 to 6, preferably from 1 to 4, carbon atoms; $C_2$–$C_{20}$—, preferably $C_2$–$C_{12}$— and most preferably $C_2$–$C_6$-alkenyl; phenyl, mono- or di-($C_1$–$C_4$-alkyl- or -alkoxy)phenyl, benzyl, mono- or di-($C_1$–$C_4$-alkyl- or -alkoxy)benzyl; or 1,2-, 1,3- or 1,4-imidazolyl-$C_1$–$C_6$alkyl, or $R_c$ and $R_d$ together are tetra- or penta-methylene, 3-oxa- 1,5-pentylene, —$CH_2$—$NR_e$—$CH_2CH_2$— or —$CH_2CH_2$—$NR_{19}$—$CH_2CH_2$— wherein $R_e$ is H or $C_1$–$C_4$alkyl. The amino group in aminoalkyl may be substituted by one or two $C_1$–$C_4$-alkyl or -hydroxyalkyl groups. The hydroxy group in hydroxyalkyl may be etherified by $C_1$–$C_4$alkyl.

Primary, secondary, tertiary and quaternary ammonium for $Y_a$ in the context of the definition of $M^\oplus$ is to be understood as being an ion of the formula $R_fR_gR_hR_iN^\oplus$ wherein $R_f$ is $C_1$–$C_{20}$—, preferably $C_1$–$C_{12}$— and most preferably $C_1$–$C_6$-alkyl, -aminoalkyl or -hydroxyalkyl; carboxyalkyl or carbalkoxyalkyl wherein the carbalkoxy group contains from 2 to 8 carbon atoms and the alkyl group from 1 to 6, preferably from 1 to 4, carbon atoms; $C_2$–$C_{20}$—, preferably $C_2$–$C_{12}$— and most preferably $C_2$–$C_6$-alkenyl; phenyl, mono- or di-($C_1$–$C_4$-alkyl- or -alkoxy)phenyl, benzyl, mono- or di-($C_1$–$C_4$-alkyl- or -alkoxy)benzyl; or 1,2-, 1,3- or 1,4-imidazolyl-$C_1$–$C_6$alkyl, and $R_g$, $R_h$ and $R_i$ are each independently of the others hydrogen or have the definition of $R_f$, or $R_f$ and $R_g$ together are tetra- or penta-methylene, 3-oxa- 1,5-pentylene, —$CH_2$—$NR_e$—$CH_2CH_2$— or —$CH_2CH_2$—$NR_e$—$CH_2CH_2$— wherein $R_e$ is H or $C_1$–$C_4$alkyl, and $R_h$ and $R_i$ each independently of the other has the definition of $R_f$. The amino group in aminoalkyl may be substituted by one or two $C_1$–$C_4$-alkyl or -hydroxyalkyl groups. The hydroxy group in hydroxyalkyl may be etherified by $C_1$–$C_4$alkyl.

Examples of carboxyalkyl are carboxymethyl, carboxyethyl, carboxypropyl and carboxybutyl, and examples of carbalkoxyalkyl are the latter carboxyalkyl groups esterified by methyl or ethyl. Examples of alkenyl are allyl, but-1-en-3-yl or 4-yl, pent-3- or -4-en-1-yl or -2-yl, hex-3- or 4- or -5-en-1-yl or -2-yl. Examples of alkyl- and alkoxy-phenyl and -benzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl and ethoxyphenyl, diethoxyphenyl, methoxybenzyl, dimethoxybenzyl, ethoxybenzyl, diethoxybenzyl. Examples of imidazolylalkyl, in which the alkyl group preferably contains from 2 to 4 carbon atoms, are 1,2-, 1,3- or 1,4-imidazolyl-ethyl or -n-propyl or -n-butyl. $R_{19}$ is preferably H, methyl or ethyl.

Preferred examples of primary amino and secondary amino are methyl-, ethyl-, dimethyl-, diethyl-, diisopropyl-, mono- or di-(1-hydroxy-eth-2-yl)-, phenyl- and benzyl-amino, acetylamino and benzoylamino and also piperidinyl, piperazinyl and morpholinyl.

Preferred examples of primary and secondary ammonium are methyl-, ethyl-, dimethyl-, diethyl-, diisopropyl-, mono- or di-(1-hydroxy-eth-2-yl)-, phenyl- and benzyl-ammonium.

Examples of $Y_a$, $R_a$ and $R_b$ as alkyl are methyl, ethyl and the isomers of propyl, butyl, pentyl, hexyl, heptyl and octyl; examples of $Y_a$, $R_a$ and $R_b$ as aryl are phenyl and naphthyl; examples of $R_a$ as alkenyl are allyl and ($C_1$–$C_4$alkyl)CH=CH—$CH_2$—; examples of $Y_a$ as aralkyl are phenyl-$C_nH_{2n}$— wherein n is a number from 1 to 6, especially benzyl; examples of $Y_a$ as alkaryl are mono-, di- and tri-($C_1$–$C_4$-alkyl)phenyl. Preferred substituents are chlorine, bromine, methoxy, —$NO_2$, —CN, 2,4-dichlorophenyl and 4-nitrophenyl. Examples of $R_b$ are 2,2,2-trichloroethyl, 4-chlorophenyl, 2-chlorophenyl and 2,4-dichlorophenyl; and examples of $R_bO$— as N-beteroaryl are pyrrol-N-yl, triazol-N-yl and benzotriazol-N-yl.

In an especially preferred form $R_a$ is β-cyanoethyl and $Y_a$ is di(isopropylamino).

When B is a purine radical or an analogue thereof, it may be a radical of formula II, IIa, IIb, IIc, IId, IIe or IIf

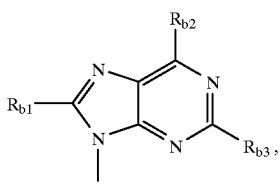

(II)

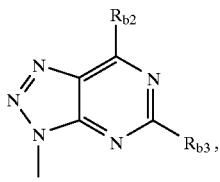

(IIa)

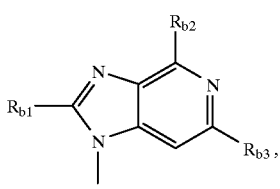

(IIb)

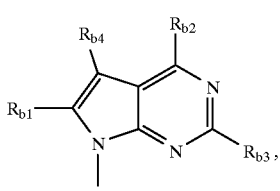

(IIc)

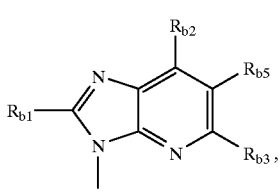

(IId)

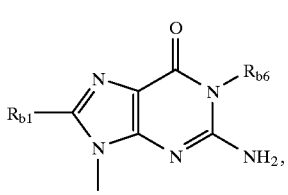

(IIe)

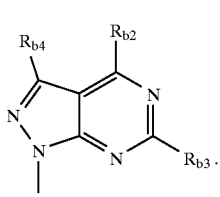

(IIf)

wherein
$R_{b1}$ is H, Cl, Br, OH or —O—$C_1$–$C_{12}$alkyl, and $R_{b2}$, $R_{b3}$ and $R_{b5}$ are each independendy of the others H, OH, SH, $NH_2$, $NHNH_2$, NHOH, NHO—$C_1$–$C_{12}$alkyl, —N═CH—N($C_1$–$C_{12}$alkyl)$_2$, —N═CH-azacycloalkyl, F, Cl, Br, $C_1$–$C_{12}$alkyl, hydroxy-$C_1$–$C_{12}$alkyl, amino-$C_1$–$C_{12}$alkyl, $C_1$–$_{12}$alkoxy, benzyloxy or $C_1$–$C_{12}$alkylthio, the hydroxy and amino groups being unsubstituted or substituted by a protecting group, phenyl, benzyl primary amino having from 1 to 20 carbon atoms or secondary amino having from 2 to 30 carbon atoms, $R_{b4}$ is hydrogen, CN or —C≡C—$R_{b7}$, and $R_{b6}$ and $R_{b7}$ are hydrogen or $C_1$–$C_4$alkyl.

Suitable protecting groups have been mentioned above. Preferred protecting groups are $C_1$–$C_8$acyl groups, such as acetyl, propionyl, butyroyl and benzoyl. $R_{b6}$ is preferably H or methyl.

The primary amino contains preferably from 1 to 12 and most preferably from 1 to 6 carbon atoms, and the secondary amino contains preferably from 2 to 12 and most preferably from 2 to 6 carbon atoms.

Some examples of alkyl, alkoxy, alkylthio, hydroxyalkyl and aminoalkyl, which preferably contain from 1 to 6 carbon atoms, are methyl, ethyl and the isomers of propyl, butyl, pentyl, hexyl, heptyl, octyl, nonyl, decyl, undecyl and dodecyl, and corresponding alkoxy, alkylthio, hydroxyalkyl and aminoalkyl radicals. Alkyl, alkoxy, alkylthio, hydroxyalkyl and aminoalkyl contain most preferably from 1 to 4 carbon atoms. Preferred alkyl, alkoxy, alkylthio, hydroxyalkyl and aminoalkyl radicals are methyl, ethyl, n- and iso-propyl, n-, iso- and tert-butyl, methoxy, ethoxy, methylthio and ethylthio, aminomethyl, aminoethyl, hydroxymethyl and hydroxyethyl.

The primary amino and secondary amino may, for example, be radicals of the formula $R_{a1}R_{a2}N$ wherein $R_{a1}$ is H or, independently, has the definition of $R_{a2}$, and $R_{a2}$ is $C_1$–$C_{20}$—, preferably $C_1$–$C_{12}$— and most preferably $C_1$–$C_6$-alkyl, -aminoalkyl or -hydroxyalkyl; carboxyalkyl or carbalkoxyalkyl wherein the carbalkoxy group contains from 2 to 8 carbon atoms and the alkyl group from 1 to 6, preferably from 1 to 4, carbon atoms; $C_2$–$C_{20}$—, preferably $C_2$–$C_{12}$— and most preferably $C_2$–$C_6$-alkenyl; phenyl, mono- or di-($C_1$–$C_4$-alkyl- or -alkoxy)phenyl, benzyl, mono- or di-($C_1$–$C_4$-alkyl- or -alkoxy)benzyl; or 1,2-, 1,3- or 1,4-imidazolyl-$C_1$–$C_6$alkyl, or $R_{a1}$ and $R_{a2}$ together are tetra- or penta-methylene, 3-oxa-1,5-pentylene, —$CH_2$—$NR_{a3}$—$CH_2CH_2$— or —$CH_2CH_2$—$NR_{a3}$—$CH_2CH_2$— wherein $R_{a3}$ is H or $C_1$–$C_4$alkyl. The amino group in aminoalkyl may be substituted by one or two $C_1$–$C_4$-alkyl or -hydroxyalkyl groups. The hydroxy group in hydroxyalkyl may be etherified by $C_1$–$C_4$alkyl.

Examples of alkyl have been given above. Examples of aminoalkyl are aminomethyl, aminoethyl, 1-aminoprop-2-yl or -3-yl, 1-amino-but-2-yl or -3-yl or 4-yl, N-methyl- or N,N-dimethyl- or N-ethyl- or N,N-diethyl- or N-2-hydroxyethyl- or N,N-di-2-hydroxyethyl-aminomethyl or -aminoethyl or -aminopropyl or -aminobutyl. Examples of hydroxyalkyl are hydroxymethyl, 1-hydroxy-eth-2-yl, 1-hydroxy-prop-2- or -3-yl, 1-hydroxybut-2-yl, -3-yl or -4-yl. Examples of carboxyalkyl are carboxymethyl, carboxyethyl, carboxypropyl and carboxybutyl, and examples of carbalkoxyalkyl are the latter carboxyalkyl groups esterified by methyl or ethyl. Examples of alkenyl are allyl, but-1-en-3-yl or -4-yl, pent-3- or 4-en-1-yl or -2-yl, hex-3- or -4- or -5-en-1-yl or -2-yl. Examples of alkyl- and alkoxy-phenyl and -benzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl and diethoxybenzyl. Examples of imidazolylalkyl, in which the alkyl group contains preferably from 2 to 4 carbon atoms, are 1,2-, 1,3- or 1,4-imidazolyl-ethyl or -n-propyl or -n-butyl. $R_{a3}$ is preferably H, methyl or ethyl.

Preferred examples of primary amino and secondary amino are methyl-, ethyl-, dimethyl-, diethyl-, allyl-, mono- or di-(1-hydroxy-eth-2-yl)-, phenyl- and benzyl-amino, acetylamino, isobutyrylamino and benzoylamino.

In a preferred form $R_{b1}$ is hydrogen. In another preferred form $R_{b5}$ is hydrogen. In yet another preferred form $R_{b2}$ and $R_{b3}$ are each independently of the other H, F, Cl, Br, OH, SH, NH2, NHOH, NHNH$_2$, methylamino, dimethylamino, benzoylamino, isobutyrylamino, methoxy, ethoxy or methylthio.

Some examples of analogues of the purine series are, apart from purine, xanthine, hypoxanthine, adenine, N-methyladenine, N-benzoyladenine, 2-methylthioadenine, 2-aminoadenine, 6-hydroxypurine, 2-amino-6-chloropurine, 2-amino-6-methylthiopurine, guanine and N-isobutyrylguanine. Especially preferred are adenine, 2-aminoadenine and guanine, and the base-protected derivatives thereof.

When B in formula I is a pyrimidine radical, it is preferably a uracil, thymine or cytosine radical of formula III, IIIa, IIIb or IIIc

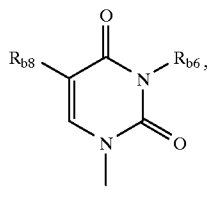

(III)

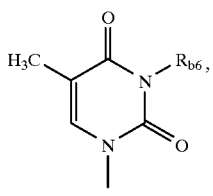

(IIIa)

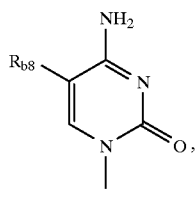

(IIIb)

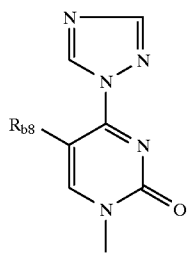

(IIIc)

wherein $R_{b6}$ is H or $C_1$–$C_4$alkyl and $R_{b8}$ is H, OH, SH, NH$_2$, NHNH$_2$, NHOH, NHO—$C_1$–$C_{12}$alkyl, —N=CH—N($C_1$–$C_{12}$alkyl)$_2$, —N=CH-azacycloalkyl, F, Cl, Br, $C_1$–$C_{12}$alkyl, hydroxy-$C_1$–$C_{12}$alkyl, amino-$C_1$–$C_{12}$alkyl, $C_1$–$C_{12}$alkoxy, benzyloxy or $C_1$–$C_{12}$alkylthio, the hydroxy and amino groups being unsubstituted or substituted by a protecting group, phenyl, benzyl, primary amino having from 1 to 20 carbon atoms, secondary amino having from 2 to 30 carbon atoms, $C_1$–$C_{12}$alkenyl or $C_1$–$C_{12}$alkynyl, and the NH$_2$ group in formula IIIb is unsubstituted or is substituted by $C_1$–$C_6$alkyl, benzoyl or by a protecting group, or a dihydro derivative of a radical of formula III, IIIa, IIIb or IIIc. Preferably, $R_{b8}$ in formula III is H, $C_1$–$C_6$-alkyl or -hydroxyalkyl, $C_2$–$C_6$-alkenyl or -alkynyl, F, Cl, Br, NH$_2$, benzoylamino, or mono- or di-$C_1$–$C_6$alkylamino. Preferably, $R_{b8}$ in formulae IIIb and IIIc is H, $C_1$–$C_6$-alkyl or -alkoxy or -hydroxyalkyl, $C_2$–$C_6$-alkenyl or -alkynyl, F, Cl, Br, NH$_2$, benzoylamino, or mono- or di-$C_1$–$C_6$alkylamino.

$R_{b6}$ is preferably H or methyl. $R_{b8}$ in formula III is preferably H, F, Cl, Br, NH$_2$, NHCH$_3$, N(CH$_3$)$_2$, $C_1$–$C_4$alkyl, $C_2$–$C_4$alkenyl or $C_1$–$C_4$alkyn-1-yl. $R_{b8}$ in formulae IIIb and IIIc is preferably H, $C_1$–$C_4$alkyl, especially methyl, $C_2$–$C_4$alkenyl, especially vinyl or $C_2$–$C_4$alkyn-1-yl, especially 1-propyn-1-yl, or NH$_2$, NHCH$_3$ or (CH$_3$)$_2$N.

Some examples of pyrimidine analogues are uracil, thymine, cytosine, 5-fluorouracil, 5-chlorouracil, 5-bromouracil, dihydrouracil, 5-methylcytosine, 5-propynethymine and 5-propynecytosine.

The invention also relates to a process for the preparation of compounds of formula I

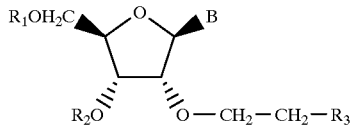

(I)

wherein $R_1$ and $R_2$ are each independently of the other hydrogen or a protecting group; and B is a purine or pyrimidine radical or an analogue thereof; and (a) $R_3$ is OH, which comprises reacting a compound of formula IVa

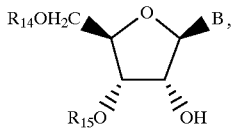

(IVa)

wherein $R_{14}$ and $R_{15}$ are identical or different protecting groups and B is a purine or pyrimidine radical or an analogue thereof and with functional groups in the base radical B being protected by protecting groups, in an inert solvent with a compound of formula A $$X—CH_2—COOR_4 \quad (A),$$

wherein $R_4$ is $C_1$–$C_4$alkyl and X is Cl, Br, I, tosyl-O or mesyl-O; and subsequently reducing the ester function with NaBH$_4$ or LiAlH$_4$, it being possible to protect the resulting OH group temporarily with a group defined for $R_1$;

(b) $R_3$ is F, which comprises reacting a compound of formula I wherein $R_3$ is OH with a compound of formula B

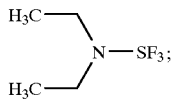

(B)

(c) $R_3$ is —(CF$_2$)$_n$—CF$_3$ wherein n is a number from 0 to 7, which comprises reacting a compound of formula IVa with a compound of formula C, D or E

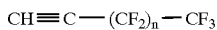 (C)

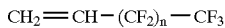 (D)

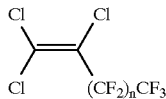 (E)

and subsequently catalytically reducing the double bond or chlorinated double bond that may be present to $CH_2CH_2(CF)_nCF_3$;

(d) $R_3$ is OH, F or —$(CF_2)_n$—$CF_3$, which comprises substituting a compound of formula IVb

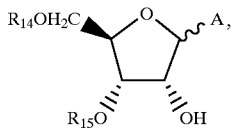 (IVb)

wherein $R_{14}$ and $R_{15}$ are as defined above and A is a leaving group, preferably alkoxy, acyloxy, mesyl-O, tosyl-O and most preferably $OCH_3$, $OCOCH_3$ or benzoyloxy, at the 2'—OH group by one of the methods described in (a) to (c) and then, in a manner known per se, introducing the base radical B by substitution [E. Lukevics, A. Zablocka, Nucleoside Synthesis, Ellis Horwood, New York (1991)]; and, if desired, removing the protecting groups $R_{14}$ and $R_{15}$.

The compounds of formulae IVa and IVb, A, B, C, D and E are known and some are available commercially or can be prepared by known or analogous methods.

Inert solvents are, for example, hydrocarbons, halogenated hydrocarbons, alkylated carboxylic acid amides and lactams, ethers, nitriles such as acetonitrile, dialkyl-sulfones or -sulfoxides or cyclic sulfones and sulfoxides.

The reaction temperatures in process steps (a) to (d) are from −50 to 200° C., preferably from 0 to 90° C.

Apart from with B, the reactions are advantageously carried out in the presence of bases, for example alkali metal hydrides, alcoholates, hydroxides or carbonates, trialkylamines or diazabicycloundecene.

Isolation of the compounds of formula I and purification thereof is carried out according to methods known per se, such as, for example, by precipitation or crystallisation and filtration and chromatographic methods.

From the compounds of formula I it is possible to build oligonucleotides that have valuable biological activities owing to their interaction with nucleic acids and that can be used as pharmaceutical active ingredients or as diagnostic agents.

The invention further relates to the use of the compounds of formula I for the preparation of oligonucleotides that comprise identical or different monomer units of compounds of formula I, but at least one monomer unit of compounds of formula I in combination with monomer units of other natural or synthetic nucleosides, the oligonucleotides comprising from 2 to 200 monomer units. The oligonucleotides comprise preferably from 2 to 100, more preferably from 2 to 50 and most preferably from 4 to 30 monomer units. Preference is given to oligonucleotides that comprise identical or different monomer units of compounds of formula I. Preference is also given to oligonucleotides that additionally comprise monomer units of synthetic or natural nucleosides derived from D-ribose or 2-deoxyribose.

The invention further relates to oligonucleotides of formula V

5'-U-(O-Y-O-V-)$_x$O-Y-O-W-3'  (V), wherein x is a number from 0 to 200 and Y is a nucleotide bridge group, U, V and W are each independently identical or different radicals of natural or synthetic nucleosides and at least one of the radicals U, V and/or W is a radical of formula VI

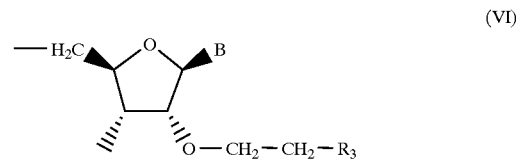 (VI)

and B and $B_3$ are as defined for the compounds of formula I, including the preferred definitions and examples.

A preferred bridge group Y is the group —$P(O)O^\ominus$— which occurs in natural oligonucleotides. Examples of other bridge groups are —$P(O)S^\ominus$—, —$P(S)S^\ominus$—, —$P(O)R_{16}$—, $P(O)NR_{17}R_{18}$ and —$CH_2$— wherein $R_{16}$ is H or $C_1$–$C_6$alkyl and $R_{17}$ and $R_{18}$ each independently of the other have the definition of $R_{16}$. In formula V, x is preferably a number from 0 to 100, more preferably a number from 1 to 50 and most preferably a number from 3 to 29. The radicals of formula VI may be bonded terminally or in the nucleotide sequence, it being possible for all or several, for example from 2 to 5, of the radicals of formula VI to follow one another, or for the radicals of formula VI to be bonded between radicals of natural or synthetic nucleosides, or for there to be mixed forms of those distributions in the nucleotide sequence.

A most especially preferred form comprises oligonucleotides of formula V wherein x is a number from 2 to 50, preferably from 2 to 30, Y is the group —$P(O)O^\ominus$—, U, V and W are each independently identical or different radicals of a natural nucleoside and at least one of the radicals U, V and W corresponds to formula VI. Suitable natural nucleosides are adenosine, cytidine, guanosine, uridine, 2-aminoadenine, 5-methylcytosine, 2'-deoxyadenosine, 2'-deoxycytidine, 2'-deoxyguanosine and thymidine. Natural nucleoside bases to be mentioned are especially adenine, cytosine, guanine, thymine and uracil. The radicals of formula VI may be bonded terminally or in the nucleotide sequence, it being possible for all or several, for example from 2 to 5, identical or different radicals of formula VI to follow one another, or for identical or different radicals of formula VI to be bonded between radicals of natural nucleosides, or for there to be mixed forms of those distributions in the nucleotide sequence. In another preferred form of oligonucleotides of formula V, all of the radicals U, V and W correspond to identical or different radicals of formula VI. x is preferably a number from 3 to 29 and preferably a total of from 1 to 12 radicals of formula VI is present.

The oligonucleotides of the invention can be prepared in a manner known per se by various methods in DNA synthesizers that may or may not be automated and that can be purchased together with instructions on procedure. In the case of the bridge group —$P(O)O^\ominus$—, for example, it is possible to use the phosphorus triester method, the phosphite triester method or the H-phosphonate method which are familiar to one skilled in the art. The procedure adopted in the case of the phosphite triester method may, for example, comprise reacting the nucleosides of formula I wherein $R_1$ and $R_2$ are each H with a protecting group reagent, for example 4,4'-dimethoxytriphenylmethyl chloride, to form a nucleoside of formula F

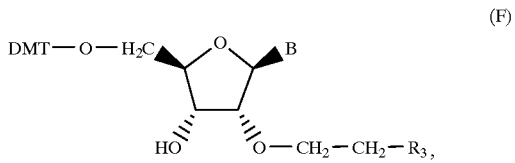

(F)

and binding the compound of formula F to a solid support, for example Controlled Pore Glass (CPG), that contains long-chained alkylamino groups, by means of a "linker", for example succinic anhydride. In a separate process, the hydroxy group of the compound of formula F is derivatised, for example to a phosphorus amidite using $R'OP[N(isopropyl)_2)]_2$, to form a compound of formula G

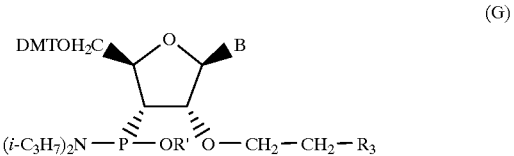

(G)

wherein R' is, for example, β-cyanoethyl.

After removal of the protecting group, such as, for example, the DMT group, of the material bound to the support, coupling to the compound of formula F is carried out with —N(iso—$C_3H_7)_2$ being removed, any free hydroxy groups present are blocked (capped) and the resulting phosphite is then oxidised to the phosphate. After de-protecting the dimer, the reaction cycle is repeated with a compound of formula G until an oligomer having the desired number of monomer units has been synthesized, and the product is detached from the support. In this manner, oligonucleotides are obtained in which all of the radicals U, V and W according to formula V consist of radicals of formula VI. It is also possible to prepare in this manner oligonucleotides having any desired monomer units in any desired sequence depending upon which synthetic and natural nucleoside units and nucleoside units according to the invention are used in the individual reaction cycles.

The compounds according to the invention of formula I wherein $_1$ and $R_2$ are each H have antiviral and antiproliferative properties and can accordingly be used as medicaments. Furthermore, the oligonucelotides according to the invention exhibit a high stability towards degradation by nucleases. Especially surprising is their excellent pairing with complementary nucleic acid strands, especially of the RNA type. In addition, they exhibit an unexpectedly high cellular uptake. The oligonucleotides according to the invention are therefore especially suitable for anti-sense technology, that is to say, for inhibiting the expression of undesired protein products by binding to suitable complementary nucleotide sequences of mRNA (EP 266 099, WO 87/07300 and WO 89/08146). They can be used for the treatment of infections and diseases, for example by blocking the expression of bioactive proteins at the nucleic acid stage (for example oncogenes). The oligonucleotides according to the invention are also suitable as diagnostic agents and can be used as gene probes for the detection of viral infections or of genetic diseases by selective interaction at the single-stranded or double-stranded nucleic acids stage. In particular—owing to the increased stability towards nucleases—their use for diagnostic purposes is possible not only in vitro but also in vivo (for example tissue samples, blood plasma and blood serum). Such possible applications are described, for example, in WO 91/06556.

The invention further relates to the use of the oligonucleotides according to the invention as diagnostic agents for the detection of viral infections or genetic diseases.

The invention also relates to the nucleosides according to the invention of the formula I and to the oligonucleotides of formula V for use in a therapeutic method for the treatment of diseases in warm-blooded animals, including man, by inactivation of the nucleotide sequences in the body. The daily dose in the case of administration to warm-blooded animals weighing approximately 70 kg may be, for example, from 0.01 to 1000 mg. Administration is effected parenterally, for example intravenously or intraperitoneally, preferably in the form of pharmaceutical compositions.

The invention further relates to a pharmaceutical composition comprising an effective amount of a nucleoside of formula I or of an oligonucleotide of formula V, on its own or together with other active ingredients, a pharmaceutical carrier, preferably in a significant amount, and, where appropriate, excipients.

The pharmacologically effective nucleosides and oligonucleotides according to the invention can be used in the form of parenterally administrable compositions or in the form of infusion solutions. Such solutions are preferably isotonic aqueous solutions or suspensions which, for example in the case of lyophilised compositions that contain the active ingredient on its own or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions, which, if desired, may comprise other pharmacologically active substances, such as antibiotics, are prepared in a manner known per se, for example by means of conventional dissolving or lyophilising processes, and comprise approximately from 0.1% to 90%, especially from approximately 0.5% to approximately 30%, for example from 1% to 5%, active ingredient(s).

The following Examples illustrate the invention. The $^1$H-NMR spectra are based on the numbering of the carbon atoms in the following cyclic carbon structures:

Starting compounds:

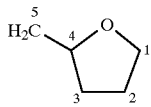

NUCLEOSIDES (EXAMPLES)

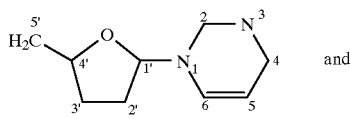

and

-continued

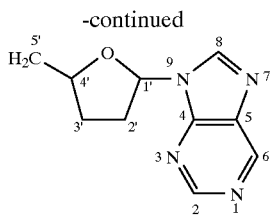

Abbreviations used in the text and in the formulae:

DMF dimethylformamide
ClBnCl₂ 2,4-dichlorobenzyl chloride
Bn benzyl
Ac acetyl
φ phenyl
BSA N,N-bistrimethylsilylacetamide
DBU diazabicyclo[5.4.0]undec-7-ene
BOM-Cl benzyloxymethyl chloride
DMTCl 4,4'-dimethoxytrityl chloride
THF tetrahydrofuran A) Preparation of nucleoside analogues

Example A1

28.0 g of 1-methylribose are added dropwise at 60° C. to a mixture of 13.5 g of NaH in 130 ml of DMF. When the evolution of H₂ has ceased, 110.0 g of ClBnCl₂ are added dropwise. The reaction mixture is stirred for a further 16 hours at 25° C. In order to destroy any NaH still present, methanol is cautiously added dropwise and the reaction mixture is then poured onto ice/water. The lumpy precipitate is filtered off and washed thoroughly with acetonitrile. Compound (A1) is obtained.

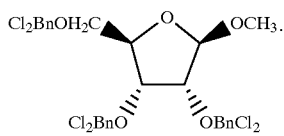

(A1)

$^1$H—NMR (250 MHz, CDCl₃): the H—C(1) proton appears at 5.0 ppm as a singlet. MS: 638 (M⁺)

Example A2

65.9 g of the product prepared in Example A1 are dissolved in 600 ml of methylene chloride and the solution is cooled to 0° C. 121 ml of SnCl₄ in 800 ml of methylene chloride are then added dropwise and the batch is left to stand at 3° C. After 26 hours, a further 2 ml of SnCl₄ are added. After a total of 35 hours, the reaction solution is cautiously poured onto 700 ml of a saturated NaHCO₃ solution. After dilution with 400 ml of methylene chloride, the Sn-containing precipitate is filtered off. The organic phase of the filtrate is dried with MgSO₄ and concentrated by evaporation to yield compound (A2).

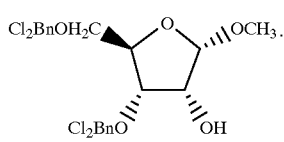

(A2)

$^1$H—NMR (250 MHz, CDCl₃): the H—C(1) proton appears at 4.90 ppm as a doublet of J=5 Hz.

Example A3

125.9 g of the product obtained in Example A2 are dissolved in 1 liter of pyridine. At 20° C., 25.5 g of acetic anhydride and 1 g of 4-dimethylaminopyridine are added. The reaction mixture is subsequently stirred for 17 hours and is then taken up in 1 liter of water, acidified with concentrated hydrochloric acid and extracted with ethyl acetate. The extract is dried with MgSO₄ and concentrated by evaporation. Finally, the residue is crystallised with hexane. Compound (A3) is obtained.

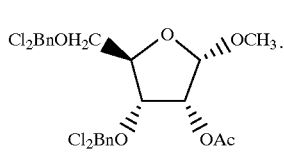

(A3)

$^1$H—NMR (250 MHz, CDCl₃): 5.15 [d, J=4.5 Hz, H—C(1)]; 3.50 (s, OCH₃); 2.17 (s, OCOCH₃); MS: 522 (M⁺) [α]$_{Na(D)}$=87.4±1.0°, CHCl₃ (0.998%)

Example A4

24 g of thymine are made into a slurry in 100 ml of 1,2-dichloroethane. After the addition of 116.4 g of BSA, the batch is heated under reflux until a clear solution is obtained. The solution is then cooled to 50° C. and 50 g of the product prepared in Example A3 and 27.5 g of trifluoromethanesulfonic acid trimethylsilyl ester are added. The batch is stirred for 20 hours at 70° C. and is then poured onto 300 ml of NaHCO₃ solution and filtered. After extraction with dichloroethane, the extract is dried with MgSO₄ and concentrated by evaporation. Finally, the residue is crystallised with methanol. Compound (A4) is obtained.

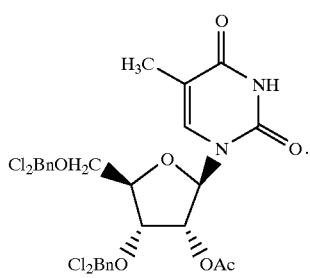

(A4)

$^1$H—NMR (250 MHz, CDCl₃): 8.25 (s, NH); 6.10 [d, J=4.5 Hz, H—C(1')]; 2.13 (s,OCOCH₃); 1.66 (s,CH₃) MS: 616 (M⁺)

Example A5

85 g of the product prepared in Example A4 are suspended in 850 ml of acetonitrile. At room temperature, 24.2 g of DBU and 24.9 g of BOM—Cl are added dropwise. After stirring for 20 hours, the reaction mixture is poured onto water and extracted with ethyl acetate. The extract is dried with MgSO$_4$ and concentrated by evaporation. Compound (A5) is obtained.

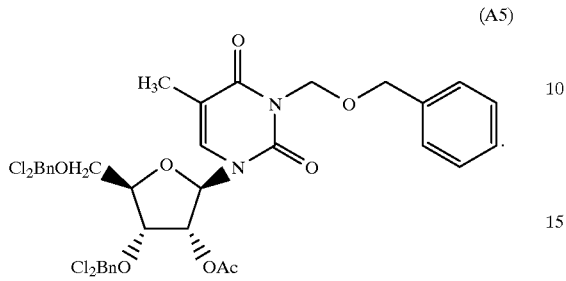

(A5)

$^1$H—NMR (250 MHz, CDCl$_3$): 6.05 [d, J=4.5 Hz, H—C(1')]; 5.5 (AB, CH$_2$); 5.37 [dd, H—C(2')]; 2.13 (s, OCOCH$_3$); 1.55 (s, CH$_3$) MS: 736 (M$^+$)

Example A6

106 g of the product prepared in Example A5 are suspended in 1 liter of THF. 26 g of a 30% NaOCH$_3$/CH$_3$OH solution are added dropwise. After stirng for 2.5 hours, the reaction solution is poured onto water, saturated aqueous sodium chloride solution is added and extraction is carried out with ethyl acetate. After drying with MgSO$_4$, the extract is concentrated by evaporation. Compound (A6) is obtained.

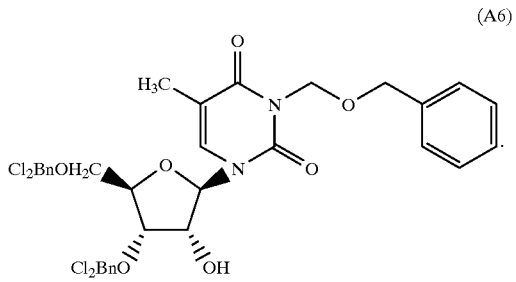

(A6)

$^1$H—NMR (250 MHz, CDCl$_3$): 5.93 [d, J=5 Hz, H—C(1')]; 5.5 (AB, CH$_2$); 3.03 (d, J=6.5 Hz, OH); 1.72 (s, CH$_3$) MS: 694 (M$^+$)

Examiple A7

79.4 g of the product obtained in Example A6 are dissolved in 800 ml of THF. After the addition of 3.3 g of NaH, the batch is boiled briefly and then, at 40° C., 21 g of bromoacetic acid methyl ester are added dropwise. The reaction mixture is stirred at 60° C. for a total of 27 hours, during which 1 g of NaH and 2 ml of bromoacetic acid methyl ester are added after 16 hours and again after 20 hours. Finally, the reaction mixture is poured onto water and extracted with ethyl acetate. The extract is dried with MgSO$_4$ and concentrated by evaporation to yield compound (A7).

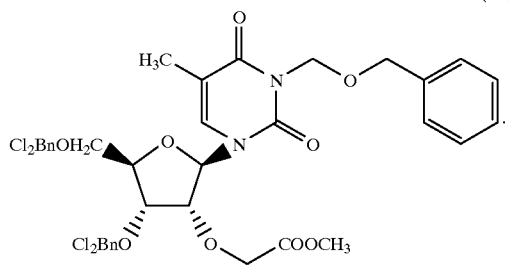

(A7)

$^1$H—NMR (250 MHz, CDCl$_3$): 7.70 [s, H—C(6)]; 5.92 [s, H—C(1')]; 5.48 (AB, CH$_2$); 3.75 (s, OCH$_3$); 1.58 (s, CH$_3$). MS: 766 (M$^+$).

Example A8

37 g of the product obtained according to Example A7 are dissolved in 400 ml of THF. At 20° C., 1.5 g of LiBH$_4$ are added in portions and the reaction mixture is stirred for 1 hour. It is then poured cautiously onto 500 ml of water and neutralised with 32 ml of 2N aqueous hydrochloric acid. After extraction with ethyl acetate and concentration by evaporation, compound (A8) is obtained.

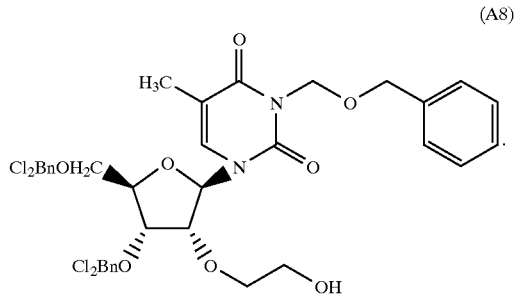

(A8)

$^1$H—NMR (250 MHz, CDCl$_3$): 7.65 [s, H—C(6)]; 5.96 [s, H—C(1')]; 5.50 (AB, CH$_2$); 2.57 (broad s, OH); 1.60 (s, CH$_3$). MS: 738 (M$^+$).

Example A9

20.0 g of the product prepared in Example A8 are dissolved in 200 ml of THF and hydrogenated over 2 g of Pd/C (5%) at 25° C. und under normal pressure for 4.5 hours (H$_2$ absorption 102%). After filtration and concentration of the filtrate by evaporation, the residue is dissolved in 170 ml of methanol and adjusted to a pH of 11 with a 30% NaOCH$_3$/CH$_3$OH solution. After 24 hours, the batch is poured onto 250 ml of water, acidified with 2N aqueous hydrochloric acid and extracted with ethyl acetate. The extract is dried with MgSO$_4$ and concentrated by evaporation. Compound (A9) is obtained.

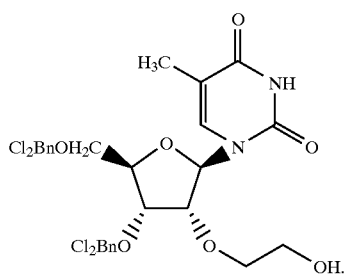

(A9)

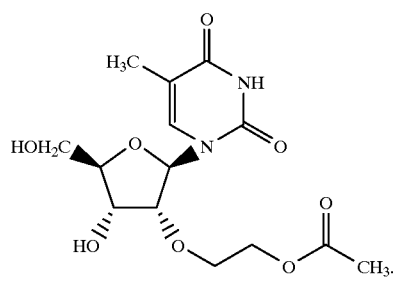

(A11)

¹H—NMR (250 MHz, CDCl₃): 9.24 (s, N$\underline{H}$); 7.90 [s, $\underline{H}$—C(6)]; 5.99 [s, $\underline{H}$—C(1')]; 2.68 (t, OH); 1.60 (s, C$\underline{H}_3$). MS: 618 (M⁺).

¹H—NMR (250 MHz, DMSO): 10.1 (s, N$\underline{H}$); 7.61 [s, $\underline{H}$—C(6)]; 5.64 [d, J=6 Hz, $\underline{H}$—C(1')]; 1.70 (s, CH₃); 1.57. MS: 379 (M+Cl)⁻.

Example A10

Example A12

4.2 g of the product prepared in Example A9 are dissolved in 50 ml of pyridine and, after the addition of 2.4 g of acetic anhydride, stirring is carried out at room temperature for 19 hours. The solution is poured onto 100 ml of 2N HCl and extracted with ethyl acetate. The extract is washed with 2N HCl and water, dried over MgSO₄ and concentrated by evaporation. Compound (A10) is obtained.

2.27 g of the product prepared in Example A11 are twice taken up in pyridine and concentrated by evaporation. The residue is again taken up in 30 ml of pyridine, and 2.57 g of DMTCl are added thereto. After stirring for 20 hours at room temperature, the reaction mixture is diluted with 250 ml of ethyl acetate and poured onto 50 ml of water. The organic phase is dried with MgSO₄ and concentrated. The residue is chromatographed on silica gel (toluene/ethyl acetate/triethylamine 49:49:2). Compound (A12) is obtained.

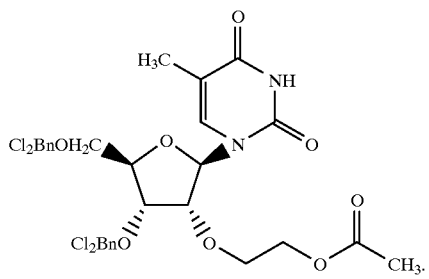

(A10)

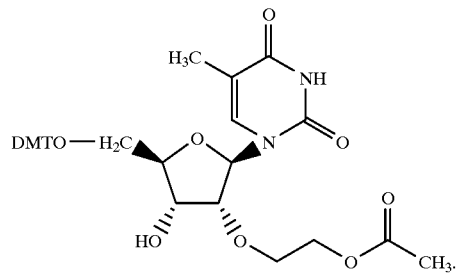

(A12)

¹H—NMR (250 MHz, CDCl₃): 9.28 (s, N$\underline{H}$); 7.67 [s, $\underline{H}$—C(6)]; 5.95 [s, $\underline{H}$—C(1')]; 2.00 (s, C$\underline{H}_3$); 1.60 (s, C$\underline{H}_3$). MS: 663 (M+H)⁺.

¹H—NMR (250 MHz, CDCl₃): 9.22 (s, NH); 7.70 [s, $\underline{H}$—C(6)]; 5.94 [d, J=1.5 Hz, $\underline{H}$—C(1')]; 3.78 (s, OC$\underline{H}_3$); 2.19 (s, C$\underline{H}_3$); 1.36 (s, C$\underline{H}_3$). MS: 706 (M+NH₄)⁺.

Example A11

Example A13

4.2 g of the product prepared in Example A10 are hydrogenated in 50 ml of methanol in the presence of 2.09 g of anhydrous sodium acetate over 0.8 g of Pd/C (5%) at 35° C. and under normal pressure. After 58 hours, the hydrogenation mixture is filtered and concentrated by evaporation. In order to remove salts, the residue is chromatographed over a small frit using silica gel (ethyl acetate/methanol 9:1). Compound (A11) is obtained.

2.70 g of the product obtained in Example A12 are added to a mixture of 0.93 g of diisopropylammonium tetrazolide, 1.51 g of 2-cyanoethyl-N,N,N',N'-tetraisopropylphosphorus diamidite and 30 ml of methylene chloride. The reaction mixture is stirred at room temperature for 17 hours and then poured onto a saturated aqueous NaHCO₃ solution. The organic phase is dried with MgSO₄ and concentrated by evaporation. The residue is chromatographed on silica gel (ethanol/ethyl acetate 1:1 with 2% addition of triethylamine). The resulting foam is dissolved in 1 ml of methyl tert-butyl ether and added dropwise at 0° C. to pentane. Compound (A13) is obtained (diastereoisomers, 1:1).

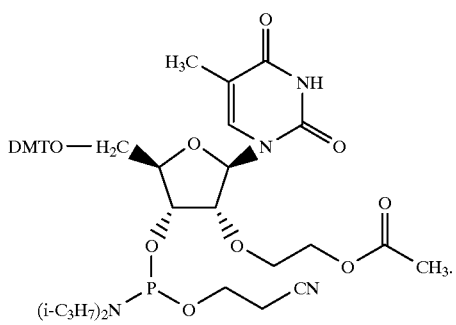

(A13)

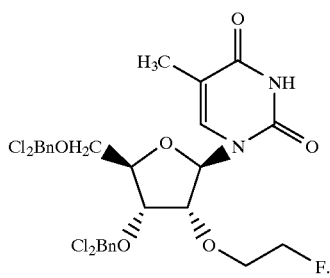

(A15)

$^1$H—NMR (250 MHz, CDCl$_3$): 7.74 [s, H—C(6)] and 7.68 [s, H—C(6)]; 6.08 [d, J=4 Hz, H—C(1')]; 5.97 [d, J=4 Hz, H—C(1')]; $^{31}$P—NMR(CDCl$_3$): 150.174 and 150.038 MS: 847 (M+H)$^+$ $^1$H—NMR (250 MHz, CDCl$_3$): 8.99 (s, NH); 7.61 [s, H—C(6)]; 5.88 [d, J=1.5 Hz, H—C(1')]; 1.52 [s, CH$_3$]. MS: 621 (M+H)$^+$.

Example A14

20.6 g of the product obtained in Example A8 are dissolved in 200 ml of CH$_2$Cl$_2$. At 5° C., 4.35 g of diethylamino-sulfur trifluoride (DAST) are added dropwise and the reaction mixture is stirred for 3 hours at 5° C. The solution is then poured onto 300 ml of saturated NaHCO$_3$ solution and extracted with CH$_2$Cl$_2$. The extract is dried over MgSO$_4$ and concentrated by evaporation. The residue is chromatographed (silica gel, toluenelethyl acetate 1:1). Compound (A14) is obtained.

Example A16

Analogously to the instructions on procedure (A11), (A12) and (A13), compound (A15) is converted into the phosphorus amidite (A16) (diastereoisomers, 1:1).

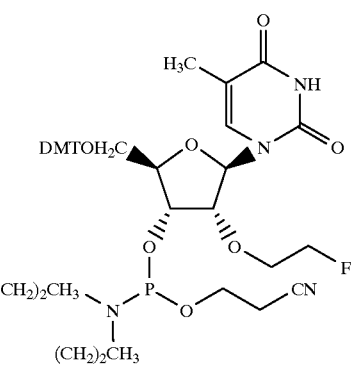

(A16)

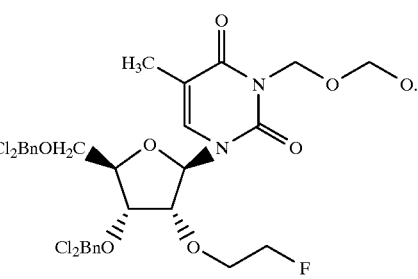

(A14)

$^1$H—NMR (250 MHz, CDCl$_3$): 7.68 [s, H—C(6)]; 5.92 [s, H—C(1')]; 5.50 [AB, CH$_2$] 1.58 (s, CH$_3$). $^{19}$F—NMR (CDCl$_3$): -223.74 (t, CH$_2$F). MS: 758 (M+NH$_4$)$^+$.

$^1$H—NMR (250 MHz, CDCl$_3$): 7.75 [s, H—C(6)] and 7.68 [s, H—C(6)]; 6.06 [d, J=4 Hz, H—C(1')] and 6.00 [d, J=4 Hz, H—C(1')]. $^{31}$P—NMR (CDCl$_3$): 150.107.

Example A15

1.30 g of the product obtained in Example A14 are dissolved in 26 ml of THF and hydrogenated over 0.65 g of Pd/C (5%) at 20° C. and under normal pressure. After 0.5 hour, the catalyst is filtered off and the filtrate is concentrated by evaporation. The residue is taken up in methanol (15 ml) and adjusted to pH 11 with NaOMe/MeOH solution. After stiring for 20 hours, the batch is poured onto 20 ml of water and extracted with ethyl acetate. After concentration by evaporation, compound (A15) is obtained.

Example A17

20.0 g of compound (A6) are dissolved in 200 ml of THF and maintained at 60° C. with 0.83 g of NaH (100%) until the evolution of H$_2$ ceases. After cooling, there are passed under pressure into this solution in an autoclave 48.0 g of trifluoropropyne and the reaction mixture is heated to 50° C. After 48 hours, the reaction mixture is concentrated to one half, then poured onto water and extracted with ethyl acetate. The extract is dried (MgSO$_4$) and concentrated by evaporation. The residue is chromatographed on silica gel (n-hexane/ethyl acetate 4:1). Compound (A17) is obtained.

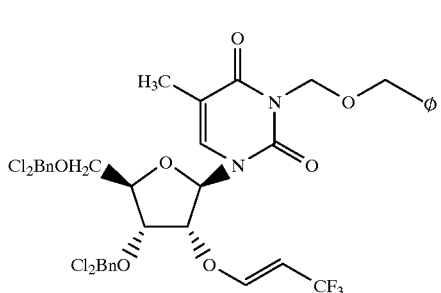

(A17)

¹H—NMR (250 MHz, CDCl₃): 7.72 [s, H—C(6)]; 6.80 (d, J=8 Hz, CH=C); 5.82 [s, H—C(1')]; 5.48 (AB, CH₂); 4.85 (m, CH=C); 1.58 (s, CH₃). MS: 789 (M+H)⁺.

Example A18

10.0 g of compound (A17) are dissolved in 200 ml of THF and hydrogenated over 2 g of Pd/C at room temperature and under normal pressure. After 1 hour, the catalyst is filtered off and the filtrate is concentrated by evaporation. The residue is subsequently treated with NaOMe analogously to Example A15 and chromatographed (silica gel; n-hexane/ethyl acetate 2:1). Compound (A18) is obtained.

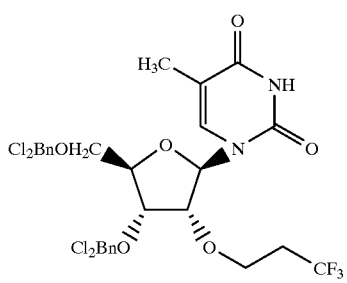

(A18)

¹H—NMR (CDCl₃): 9.00 (s, NH); 7.66 [s, H—C(6)]; 5.93 [d, J=1.5 Hz, H—C(1')]; 1.61 (s, CH₃). ¹⁹F—NMR (CDCl₃): −65.23. MS: 705 (M+Cl)⁻.

Example A19

8.9 g of compound (A6) are dissolved in 90 ml of THF and boiled briefly with 0.34 g of NaH (100%). When the evolution of H₂ has ceased, 5.1 g of 1,1,2-trichloro-3,3,3-trifluoropropene are added dropwise at 20° C. and the reaction mixture is then stirred at 55° C. for 5 hours. The reaction mixture is poured onto water and extracted with ethyl acetate. Concentration by evaporation is followed by chromatography (silica gel, toluene/ethyl acetate 4:1). Compound (A19) is obtained in the form of a cis/trans (approx. 1:1) mixture.

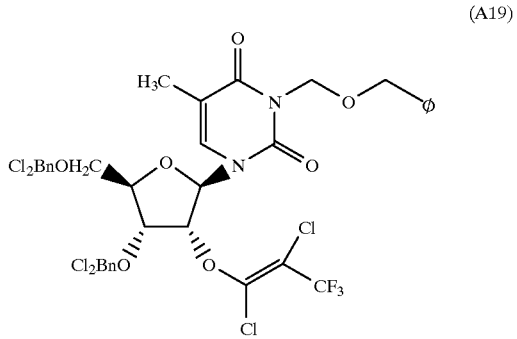

(A19)

¹H—NMR (CDCl₃): 7.63 and 7.60 [each s, each H—C(6)]; 5.91 and 5.87 [each s, each H—C(1')]; 1.61 and 1.57 (each s, each CH₃). MS: 891 (M+Cl)⁻.

Example A20

If compound (A18) or (A19) is deprotected analogously to the above Examples and converted into the phosphorus amidite, compound (A20) (diastereoisomers 1:1) is obtained.

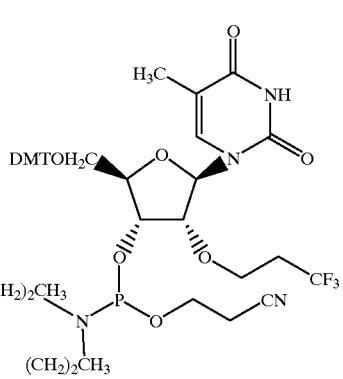

(A20)

¹H—NMR (CDCl₃): 8.6 (broad s, NH); 7.74 and 7.69 [each s, each H—C(6)]; 5.97 and 5.94 [each d, J=4 Hz, each H—C(1')]. ³¹P—NMR (CDCl₃): 150.287 and 150.035 ppm.

Example B

Preparation of oligonucleotides

Oligonucleotides are bound to a solid support (Controlled Pore Glass, CPG) using the dimethoxytritylated and 3'-activated [3'-(β-cyanoethoxy-di(isopropylamino) phosphoramidite)] nucleosides according to the invention and such natural activated nucleosides and the synthesis is carried out in a DNA-synthesizer (Applied Biosystems, Modell 380 B, standard phosphorus amidite chemistry and iodoxidation) following the standard instructions of the manufacturer [see also "Oligonucleotide synthesis, a practical approach" M. J. Gait; IRL Press 1984 (Oxford-Washington D.C.)]. After coupling of the last nucleoside unit, the 5'-protected oligonucleotide is detached from the carrier overnight, while simultaneously removing all the other protecting groups, by treatment with concentrated aqueous ammonia, and is then purified by reversed phase HPLC using 50 mM ammonium acetate buffer (pH 7)/acetonitrile. The 5'-dimethoxytrityl protecting group is then removed by treating for 20 minutes with 80% aqueous acetic acid, and the oligonucleotide is precipitated with ethanol and isolated by centrifugation. The purity of the oligonucleotide is verified by gel electrophoresis (polyacrylamide) and its identity by means of matrix-assisted laser desorption time-of-flight mass spectroscopy (MALDI-TOF MS).

Example C1

Affinity; interaction of the oligonucleotides (anti-sense) with complementary oligoribonucleotide sequences (sense)

The interaction of the oligonucleotides with the corresponding base-complementary oligomers of natural ribonucleotides is characterised by recording UV melt curves and the $T_m$ values determined therefrom. This standard method is described, for example, by Marky, L. A., Breslauer, K. J., Biopolymers 26:1601–1620 (1987).

A solution of the oligonucleotides and the corresponding base-complementary natural oligoribonucleotides in 10 mM phosphate buffer, 100 mM NaCl, 0.1 mM EDTA, pH=7.0 (c=4.10$^{-6}$ M/oligonucleotide) is prepared and the change in the extinction at 260 nm as a function of the temperature (15 to 95° C.) is recorded. From the melt curves obtained the $T_m$ value is determined (Table 3).

TABLE 3

| Affinity | | |
|---|---|---|
| (a) TTTTtCTCTCTCTCT (vs. RNA) | | |

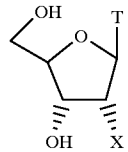

| X | Tm (° C.) | ΔTm (° C.) |
|---|---|---|
| H | 51.8 | 0 |
| 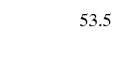 | 53.1 | +1.3 |
| 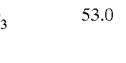 | 53.5 | +1.7 |
| 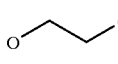 | 53.0 | +1.2 |

TABLE 3-continued

| Affinity | | |
|---|---|---|
| 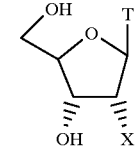 | 53.0 | +1.2 |

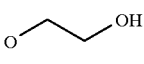

| X | Tm (° C.) | ΔTm (° C.)/mod. |
|---|---|---|
| (b) tCCAGGtGtCCGCAtC (vs. RNA) | | |
| H | 62.3 | 0 |
| 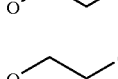 | 70.5 | +1.0 |
| 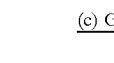 | 68.0 | +1.4 |
| 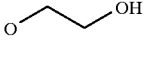 | 65.1 | +0.7 |
| (c) GCGttttttttttGCG (vs. RNA) | | |
| H | 50.2 | 0 |
| 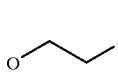 | 62.4 | +1.2 |
|  | 61.9 | +1.2 |
| 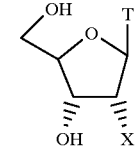 | 58.1 | +0.8 |

Example D2

Specificity; Interaction of the oligonucleotide with base-complementary oligoribonucleotides in which an incorrect nucleoside (Y) has been inserted Solutions of the oligonucleotide with the corresponding base-complementary oligonucleotides having the sequences r(GGA CCG GAA YGG TAC GAG) in 10 mM phosphate buffer, 100 mM NaCl, 0.1 mM EDTA, pH 7, (c=4.10$^{-6}$ M/oligonucleotide) are prepared and the change in the extinction at 260 nm as a function of the temperature (15° C. to 95° C.) is measured. From the curves the $T_m$ value is determined. The results are shown in Table 4.

TABLE 4

Specificity
sense: 3'-GAG CAU GGY AAG GCC AGG-5' (RNA)
anti: 5'-CTC GTA CCt TTC CGG TCC-3' (DNA)
Tm(° C.) and ΔTm

|  | OH, T (OH, H) | OH, T (OH, O-CH2CH2-F) | OH, T (OH, O-CH2CH2-CH3) |
|---|---|---|---|
| Y = A | 63.3 | 65.0 | 69.4 |
| Y = C | 54.5 | 55.5 | 55.8 |
|  | (−8.9) | (−9.5) | (−8.6) |
| Y = G | 61.6 | 59.7 | 60.5 |
|  | (−1.7) | (−5.3) | (−4.0) |
| Y = U | 55.8 | 56.2 | 56.8 |
|  | (−7.5) | (−8.8) | (−7.7) |
| Y = none | 59.4 | 56.1 | 57.4 |
|  | (−3.9) | (−8.9) | (−7.0) |

Example C3

Nuclease-stability; enzymatic hydrolysis of various oligonucleotides having the sequence d(TCC AGG TGT CCG ttt C)

Batches of the synthetic oligonucleotide and of the corresponding natural oligomer, each of 14 μg, are incubated in 200 μl of 10% heat-inactivated foetal calf serum at 37° C. (c=70 μg/ml). After 0.5; 1; 2; 4; 6, 24 and 48 hours, 15 μl of each reaction solution are quenched by being added to 25 μl of 9M urea and trisborate buffer (pH 7) and stored at −20° C. until the measurement is carried out. The quenched reaction solutions are separated by means of polyacrylamide gel electrophoresis and the cleavage products are identified by their phosphorus content (phospho-imager method). The ratio R of the sum of the concentrations of the completely intact oligonucleotide ($c_n^{(t)}$) and of the fragment ($c_{n-1}^{(t)}$), obtained by removing the natural C-unit from the 3' end, at a given time t to the original concentration of the completely intact oligonucleotide at the point t=0 ($c_n^{(0)}$) R=($c_n^{(t)}$+$c_{n-1}^{(t)}$)/$c_n^{(0)}$ is plotted on a graph against time. The half-times $\tau_{1/2}$—that is to say, those times for which R=0.5—so determined are:

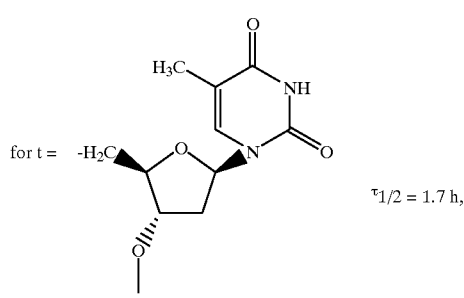

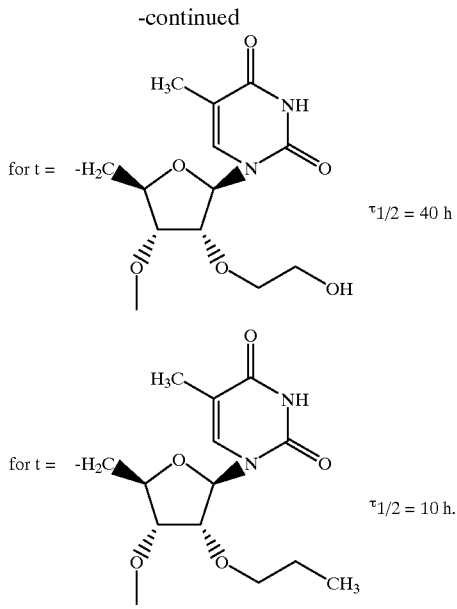

What is claimed is:

1. An oligonucleotide of formula V $$5'-U-(O-Y-O-V-)_x O-Y-O-W-3' \quad (V),$$

wherein x is a number from 0 to 200 and

Y is a nucleotide bridge group;

U, V and W are each independently identical or different radicals of natural or synthetic nucleosides and at least one of the radicals U. V and/or W is a radical of formula VI

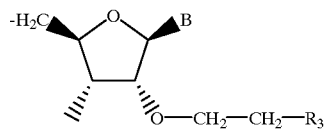

wherein

B is a purine or pyrimidine radical or a heterocyclic analogue thereof and $R_3$ is OH or F.

2. An oligonucleotide according to claim 1, wherein the bridge group Y is —P(O)O$^\ominus$—, —P(O)S$^\ominus$—, —P(S)S$^\ominus$—, —P(O)R$_{16}$—, —P(O)NR$_{17}$R$_{18}$— or —CH$_2$— wherein R$_{16}$ is H or C$_1$–C$_6$alkyl and R$_{17}$ and R$_{18}$ each independently of the other have the definition of R$_{16}$.

3. An oligonucleotide according to claim 1, wherein the bridge group Y is —P(O)O$_\ominus$—.

4. An oligonucleotide according to claim 1, wherein x is a number from 0 to 100.

5. An oligonucleotide according to claim 4, wherein x is a number from 1 to 50.

6. An oligonucleotide according to claim 5, wherein x is a number from 3 to 29.

7. An oligonucleotide according to claim 1, wherein the radicals of formula VI are bonded between radicals of natural or synthetic nucleosides.

8. An oligonucleotide according to claims 1 and 7, wherein from 2 to 5 identical or different radicals of formula VI follow one another.

9. An oligonucleotide according to claim 1, wherein a total of from 4 to 30 nucleoside units and from 1 to 12 radicals of formula VI is present.

10. An oligonucleotide according to claim 1, wherein B as a purine radical or an analogue thereof is a radical of formula II, IIa, IIb, IIc, IId, IIe or IIf

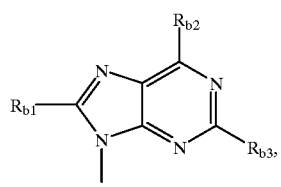

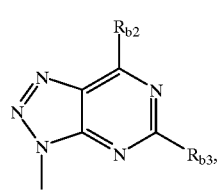

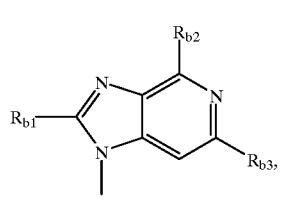

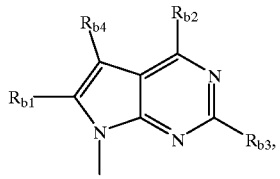

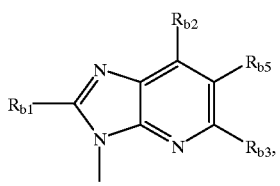

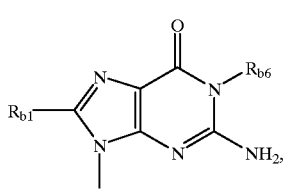

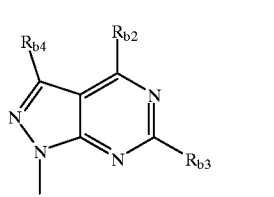

wherein $R_{b1}$ is H, Cl, Br, OH or —O—C$_1$–C$_{12}$alkyl, and $R_{b2}$, $R_{b3}$ and $R_{b5}$ are each independently of the others H, OH, SH, NH$_2$, NHNH$_2$, NHOH, NHO—C$_1$–C$_{12}$alkyl, —N=CH—N(C$_1$–C$_{12}$alkyl)$_2$, —N=CH—N-cycloaLkyl, F, Cl, Br, C$_1$–C$_{12}$alkyl, hydroxy-C$_1$–C$_{12}$alkyl, amino-C$_1$–C$_{12}$alkyl, C$_1$–C$_{12}$alkoxy, benzyloxy or C$_1$–C$_{12}$alkylthio, the hydroxy and amino groups being unsubstituted or substituted by a protecting group, phenyl, benzyl, primary amino having from 1 to 20 carbon atoms or secondary amino having from 2 to 30 carbon atoms, $R_{b4}$ is hydrogen, CN or —C≡C—R$_{b7}$, and $R_{b6}$ and $R_{b7}$ are hydrogen or C$_1$–C$_4$alkyl.

11. An oligonucleotide according to claim 1, wherein B is a uracil, thymine or cytosine radical of formula III, IIIa, IIIb or IIIc

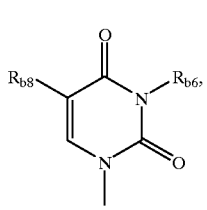

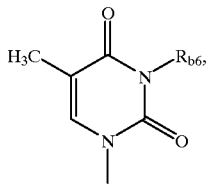
(IIIa)

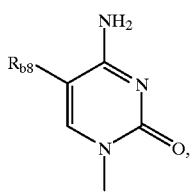
(IIIb)

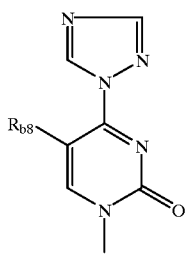
(IIIc)

wherein $R_{b6}$ is H or $C_1$–$C_4$alkyl and $R_{b8}$ is H, OH, SH, $NH_2$, $NHNH_2$, NHOH, NHO—$C_1$–$C_{12}$alkyl, —N=CH—N($C_1$–$C_{12}$alkyl)$_2$, —N=CH—N-cycloalkyl, F, Cl, Br, $C_1$–$C_{12}$alkyl, hydroxy-$C_1$–$C_{12}$alkyl, amino-$C_1$–$C_{12}$alkyl, $C_1$–$C_{12}$alkoxy, benzyloxy or $C_1$–$C_{12}$alkylthio, the hydroxy and amino groups being unsubstituted or substituted by a protecting group, phenyl, benzyl, primary amino having from 1 to 20 carbon atoms, secondary amino having from 2 to 30 carbon atoms, $C_1$–$C_{12}$alkenyl or $C_1$–$C_{12}$alkynyl, and the $NH_2$ group in formula IIIb is unsubstituted or is substituted by $C_1$–$C_6$alkyl, benzoyl or by a protecting group, or a dihydro derivative of a radical of formula III, IIIa, IIIb or IIIc.

12. An oligonucleotide according to claim 1, wherein $R_3$ is OH.

13. An oligonucleotide according to claim 1, wherein $R_3$ is F.

14. A composition comprising an oligonucleotide of formula V according to claim 1 and an inert carrier.

* * * * *

UNITED STATES PATENT AND TRADEMARK OFFICE
CERTIFICATE OF CORRECTION

PATENT NO : 5,977,332
DATED: : November 2, 1999
INVENTOR(S) : MARTIN.

It is certified that there is an error in the above-identified patent and that said Letters Patent is hereby corrected as shown below:

Claim 3, in column 27, second line of the said claim should read:

-- bridge group Y is $-P(O)O^{\ominus}-$. --.

Claim 8, in column 27, first line of said claim should read:

-- An oligonucleotide according to claims 1 or 7, --.

Claim 10, in column 28, line 44 should read:

-- cycloalkyl, F, Cl, Br, $C_1$-$C_{12}$aklyl, hydroxy- --.

Signed and Sealed this

Third Day of April, 2001

*Attest:*

NICHOLAS P. GODICI

*Attesting Officer*     *Acting Director of the United States Patent and Trademark Office*